United States Patent [19]

Miyasaka et al.

[11] Patent Number: 4,813,423
[45] Date of Patent: Mar. 21, 1989

[54] INSTRUMENT FOR MEASURING LIVING BODY COMPONENTS

[75] Inventors: Katsuyuki Miyasaka, Tokyo; Masao Katayama, Sagamihara; Hisayoshi Yamamori; Teruyoshi Uchida, both of Nagoya; Junichi Tashita, Yokohama; Akihiko Ooe, Komaki; Youjirou Watanabe, Nagoya, all of Japan

[73] Assignee: Mitsubishi Rayon Company Ltd., Tokyo, Japan

[21] Appl. No.: 52,903

[22] Filed: May 22, 1987

[30] Foreign Application Priority Data

Dec. 23, 1986 [JP] Japan .................... 61-306870

[51] Int. Cl.⁴ .................................... A61B 5/00
[52] U.S. Cl. .......................... 128/634; 128/673; 128/692
[58] Field of Search ............ 128/634, 632, 692, 673; 604/266 X

[56] References Cited

U.S. PATENT DOCUMENTS 4,442,841  4/1984  Uehara et al. .............. 126/635
4,622,974  11/1988  Coleman et al. ........... 128/634
4,736,748  4/1988  Nakamura et al. ......... 128/632

FOREIGN PATENT DOCUMENTS 1402742  9/1972  United Kingdom ......... 128/673

*Primary Examiner*—William E. Wayner
*Attorney, Agent, or Firm*—Oblon, Fisher, Spivak, McClelland & Maier

[57] ABSTRACT

Disclosed is an instrument for measuring living body components, which has (i) a fine tube having at one end thereof a connection portion to be connected to an indwelling needle or indwelling catheter and an infusion portion, from which at least a blood anticoagulant solution can be infused, (ii) a fine linear sensor for measuring living body components, extended from the inferior of the fine tube to the outside through the connection portion, and (iii) a mechanism for introducing blood at least into the interior of a fine tube portion of the indwelling needle or catheter intermittently or periodically when the indwelling needle or catheter is connected to the fine tube and kept in the blood vessel and then discharging blood into the blood vessel. A sensing portion of the sensor is located within the fine tube portion of the indwelling needle or catheter when the indwelling needle or catheter is connected to the connection portion of the fine tube.

6 Claims, 1 Drawing Sheet

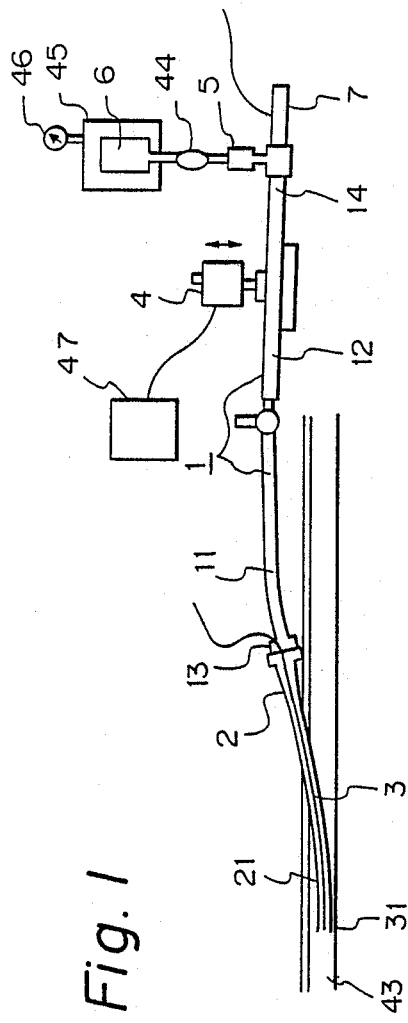
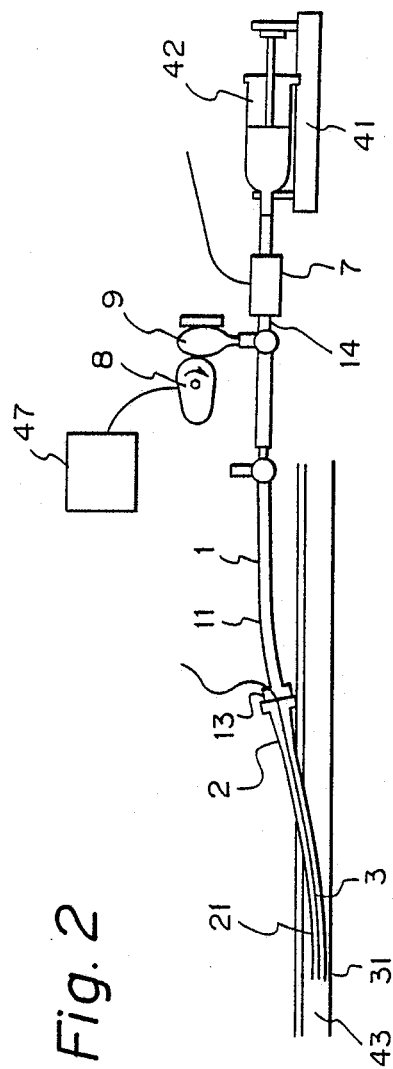

INSTRUMENT FOR MEASURING LIVING BODY COMPONENTS

BACKGROUND OF THE INVENTION (1) Field of the Invention

The present invention relates to an instrument for measuring living body components, which is inserted and kept in the blood vessel and can measure living body components with a high accuracy.

(2) Description of the Related Art

As means for measuring blood gas components such as the oxygen partial pressure, the carbon dioxide gas partial pressure, the pH value and the saturated oxygen concentration in blood, and components contained in blood, such as potassium, sodium, calcium, glucose, lactic acid and urea, a method is generally adopted in which blood is collected and the measurement is performed by using a living body component analyzer. However, this method has a problem in that every time it is desired to know the state of blood components, blood must be collected from a patient and analyzed and it is difficult to determine the state of the patient from moment to moment. In addition, it is impossible to determine real-time changes of the living body components in a continuous manner. Recently, the significance of a continuous measurement of living body components has been recognized and the demand for this continuous measurement has increased. As a means for satisfying this demand, there has been tried a method in which a sensor for measuring living body components is directly inserted into the blood vessel by using an indwelling needle, an indwelling catheter or the like and is kept in the blood vessel to continuously measure the living body components.

In the method in which the measurement is carried out in the state where the sensor is kept in the blood vessel, often the measured value is different from the value obtained by analyzing blood taken from the living body, and the measurement is not performed stably with good reliability. In this method, a solution of blood anticoagulant is supplied from the indwelling needle or indwelling catheter to prevent coagulation of the blood. If the amount of the blood anticoagulant is small, the adhesion of coagulation products of blood to the sensing portion of the sensor cannot be sufficiently prevented and this adhesion results in a reduction of the measurement accuracy. Moreover, coagulation of the blood in the blood vessel is dangerous to the patient. If the blood anticoagulant is administered in an amount sufficient to prevent this adhesion, often the patient is adversely influenced. Accordingly, it is difficult to maintain a good balance between the amount of the blood anticoagulant administered and the adhesion-preventing effect.

SUMMARY OF THE INVENTION

The inventors carried out research with a view to preventing the occurrence of these undesirable phenomena, and as a result, found that when the sensing portion of the sensor for measuring living body components, which is kept in the blood vessel, comes into touch with the wall of the blood vessel, the state of the surroundings of the sensing portion of the sensor is changed from the state where the sensing portion is held in blood, and an error is caused by this change of the state. It also was found that, when the sensing portion of the sensor is located outside of the indwelling needle, it is difficult to supply a sufficient amount of the blood anticoagulant to the surroundings of the sensing portion and therefore, blood is readily coagulated on the surface of the sensing portion. Various measures were examined for coping with these disadvantages and success occurred in fabricating an instrument for measuring living body components, which is superior in that the above-mentioned error rarely occurs and the adhesion of blood or proteins to the sensing portion of the sensor and the coagulation of the blood can be substantially prevented.

More specifically, in accordance with the present invention, there is provided an instrument for measuring living body components, which comprises a fine tube having at one end thereof a connection portion to be connected to an indwelling needle or indwelling catheter and an injection portion, from which at least a solution of a blood anticoagulant can be injected, a fine linear sensor for measuring living body components, which is extended from the interior of the fine tube to the outside through the connection portion, and a mechanism for introducing blood at least into the interior of a fine tube portion of the indwelling needle or indwelling catheter intermittently or periodically when the indwelling needle or indwelling catheter is connected to the fine tube and kept in the blood vessel and then discharging blood into the blood vessel, wherein a sensing portion of the sensor is located within the fine tube portion of the indwelling needle or indwelling catheter when the indwelling needle or indwelling catheter is connected to the connection portion of the fine tube.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 1 is a diagram illustrating an embodiment of the living body component-measuring instrument of the present invention in the state where the indwelling needle and the liquid infusion mechanism are connected to the tube; and FIG. 2 is a diagram illustrating another embodiment of the instrument of the present invention.

DESCRIPTION OF THE PREFERRED EMBODIMENTS

As the living body component-measuring sensor used in the present invention, there can be mentioned blood gas-related sensors for measuring the oxygen partial pressure, the carbon dioxide gas partial pressure, the pH value, the saturated oxygen concentration or the like, ion sensors for measuring potassium, sodium, calcium or the like, sensors for measuring blood plasma components such as glucose, lactic acid or urea, and sensors for measuring concentrations in the blood of medicines such as vasodilators, digitalis or antibiotics. Either a sensor for measuring a single component or a multi-sensor for measuring a plurality of components can be used. The detection method adopted in the sensor is not particularly critical, and any of an electrochemical method, a method utilizing light and a method using a field effect transistor can be adopted. In short, any fine linear sensor which can be inserted and kept in the blood vessel through an indwelling needle or indwelling catheter can be used in the present invention.

The fine tube used in the present invention has at one end thereof a connection portion that can be connected to an indwelling needle or indwelling catheter and an infusion portion, from which at least a solution of a blood anticoagulant can be infused. A fine linear sensor for measuring the living body components, which is extended to the outside from the fine tube through the connection portion, is contained in the fine tube. As the fine tube, there can be mentioned, for example, an ordinary extension tube, a combination of a plurality of extension tubes, and a combination of an extension tube and other fine tubes. The sensing portion of the sensor must be located within a fine tube portion of the indwelling needle or indwelling catheter when the indwelling needle or indwelling catheter is connected to the connecting portion of the fine tube. If the sensing portion of the sensor is located ahead of the top end of the indwelling needle or indwelling catheter, the sensing portion comes into touch with the wall of the blood vessel or coagulation products of the blood adhere to the sensing portion, and thus, an abnormal measurement result is obtained and a sufficiently high accuracy cannot be expected. In contrast, if the sensing portion is excessively intruded into the interior of the indwelling needle or indwelling catheter and is located in the vicinity of a connecting portion of the fine tube, a problem readily occurs in connecting the fine tube to the indwelling needle or indwelling catheter. Accordingly, preferably the sensing portion of the sensor located within the fine tube portion of the indwelling needle or indwelling catheter is present at a point distant by 10 mm or less from the top end of the indwelling needle or indwelling catheter. By the fine tube portion of the indwelling needle or indwelling catheter is meant a tube portion of the indwelling needle or indwelling catheter which is finer than the connection portion, and this portion is kept in the patient body when the indwelling needle or indwelling catheter is kept in the blood vessel. If the sensing portion of the sensor is located within the fine tube portion, the sensing portion is not influenced by the environmental temperature and an effect of increasing the measurement accuracy is attained.

In the living body component-measuring instrument of the present invention having the above-mentioned structure, a solution of a blood anticoagulant such as heparin should be infused at a constant rate from the infusion portion to prevent blood from coagulating and adhering to the indwelling needle or indwelling catheter or the sensing portion of the living body component-measuring sensor while the instrument is used. Accordingly, in this arrangement, the sensing portion of the sensor comes into contact only with the blood anticoagulant solution and a sufficient content with the blood is not realized. Therefore, the instrument must be provided with a mechanism for introducing blood at least into the interior of the fine tube portion of the indwelling needle or indwelling catheter intermittently or periodically when the indwelling needle or indwelling catheter is connected to the fine tube and is kept in the blood vessel and then discharging blood into the blood vessel.

As the mechanism for introducing blood at least into the interior of the fine tube portion of the indwelling needle or indwelling catheter intermittently or periodically and then discharging blood into the blood vessel, there can be used any mechanism having functions such that the inner volume of the fine tube or the space connected to the fine tube and filled with the blood anticoagulant solution is changed to cause the blood anticoagulant solution in the top end portion of the indwelling needle or indwelling catheter to flow back toward the interior and cause the blood in the blood vessel to flow into the indwelling needle or indwelling catheter and the blood is substantially in touch with the surface of the sensing portion of the sensor within the fine tube portion. As a preferred example of this mechanism, there can be mentioned a mechanism for intermittently or periodically applying a pressure to the wall of the fine tube and releasing said pressure, at least a part of the wall of the fine tube having an elasticity such that said part of the wall is deformed under application of an external pressure and the original shape of said part of the wall is restored when an external pressure different from said external pressure is applied or said external pressure is released. As another preferred example of the mechanism, there can be mentioned a mechanism comprising a volume-variable hollow portion connected only to the interior of the fine tube and a mechanism for applying a pressure to said hollow portion and releasing that pressure. This hollow portion may be defined by a balloon having an elastic wall or an injection syringe. Moreover, there may be adopted a mechanism comprising an injection syringe attached to an infusion pump for driving the syringe in both the normal and reverse direction, in which the blood anticoagulant solution is introduced and returned repeatedly. In this case, the introduced amount should be larger than the return amount in each cycle.

As the elastic material constituting the fine tube or balloon, there can be mentioned various rubbers such as a silicone rubber, and polyethylene, non-rigid polyvinyl chloride and polyamides. Of course, the material that can be used is not limited to these materials and any medically acceptable elastic material can be utilized in the present invention.

The end opposite to the side of the sensing portion of the living body component-measuring sensor used in the present invention should be exposed over the fine tube for connection to an apparatus for reading and displaying signals emitted from the sensing portion. For example, a method may be adopted in which an opening is formed in the side wall of the fine tube, the end of the sensor is taken out from the opening, and the opening is sealed with an appropriate sealant to fix the sensor, or a method in which the end, opposite to the side of the sensing portion, of the sensor is taken out through an opening such as the injection portion. In short, it is sufficient if only said end is taken out to the outside without a leakage of the blood or the blood anticoagulant solution.

The present invention will now be described in detail with reference to the accompanying drawings.

FIG. 1 is a diagram illustrating the state where an indwelling needle and a liquid pouring mechanism are attached to one embodiment of the living body component-measuring instrument of the present invention. FIG. 2 is a diagram illustrating another embodiment of the present invention. In the embodiment illustrated in FIG. 1, the mechanism for introducing blood at least into a fine tube portion 21 of an indwelling needle or indwelling catheter 2 intermittently or periodically when the indwelling needle or indwelling catheter 2 is connected to a fine tube 1 and then discharging blood into the blood vessel is a mechanism for intermittently or periodically pressing and unpressing a wall of the fine tube 1, at least a part of which has an elasticity such that said part of the wall is deformed by an external pressure and the original shape is restored under application of a pressure lower than said external pressure or when said external pressure is released. As a means for pressing the wall intermittently or periodically, there can be adopted, as shown in FIG. 1, a device 4 performing a piston motion, or an eccentric cam 8 (see FIG. 2). Moreover, the fine tube may be bent and stretched to change the inner volume of the fine tube.

In the embodiment shown in FIG. 2, the above-mentioned mechanism comprises an inner volume-variable hollow portion connected only to the interior of the fine tube and a mechanism for applying a pressure to the hollow portion and releasing at least a part of the pressure, and a balloon 9 is used as the inner volume-variable hollow portion. An injection syringe may be used instead of the balloon. A mechanism similar to the above-mentioned mechanism for pressing the fine tube can be adopted as the pressure-applying mechanism. Furthermore, a pneumatic pressure can be used. Instead of the method using the balloon, a method may be adopted in which injection of the blood anticoagulant solution is effected by an infusion pump 41 and an injection syringe 42 in combination and the blood anticoagulant solution is injected and is caused to flow backward. From the purpose of the present invention, it will be understood that a subatmospheric pressure can be used as the pressure to be applied.

The function exerted when the instrument of the present invention is used will now be described with reference to FIG. 1. After the indwelling needle 42 is inserted and kept in the blood vessel 43, the indwelling needle 2 is connected to the connection portion 13 of the fine tube 1 of the instrument of the present invention. An I.V. solution bag 6 is connected to the top of the infusion portion 14 of the fine tube through a high-resistance tube 5, and the blood anticoagulant solution is continuously infused at a constant rate. Accordingly, the blood anticoagulant solution or a mixture thereof with blood is present around the living body component-measuring sensor 3, and thus, coagulation of blood on the surface of the sensor or adhesion of proteins to the surface of the sensor can be minimized, with the result that the probability of occurrence of an error is greatly reduced. It is sufficient if the rate of infusing the blood anticoagulant solution is 0.5 to several ml/hr, and of course, a higher injection rate may be adopted. Preferably the supply pressure of the blood anticoagulant solution be about 300 mmHg, but various pressures may be set according to need.

The fine tube is pressed by the piston movement device 4 periodically or intermittently to deform the fine tube at least partially, whereby the blood anticoagulant solution is pushed out from the indwelling needle. If the pressure is then released, since the blood anticoagulant solution is not sufficiently infused, blood in the blood vessel 43 is introduced into the indwelling needle 2. As the piston movement device, there can be mentioned, for example, a device in which a shaft is vertically moved by using a solenoid.

It is sufficient if the amount of introduced blood is such that blood reaches the sensing portion 31 of the blood component-measuring sensor 3 which is present in the fine tube portion of the indwelling needle, and the amount of introduced blood need not exceed this level. If blood is introduced in too large an amount, a long time is required for substitution of the introduced blood with the blood anticoagulant solution and for example, in order to improve the response characteristic, a relatively large amount of blood must be introduced and discharged at a high speed.

Preferably the amount of introduced blood is adjusted so that blood gas beyond the indwelling needle but does reach the fine tube 1.

This adjustment of the amount of introduced blood is accomplished by appropriately controlling the volumes of the indwelling needle and its top end portion (from the top end of the sensing portion of the sensor), the infusion rate of the blood anticoagulant solution and the rate and quantity of the change of the inner volume of the fine tube caused when the deformed fine tube is restored to its original shape.

The present invention will now be described in detail with reference to the following examples.

EXAMPLE 1

An electrode (living body component-measuring sensor 3) comprising a platinum wire having a diameter of 150 $\mu$m and having the periphery covered with an insulating coating layer and the top end covered with a porous polyurethane membrane was inserted into an extension tube having at one end a connection portion 13 to be connected to an indwelling needle and a three-way stop cock at the other end, so that when the top end of the electrode was extended from the connection portion 13 and an indwelling needle 2 (Surflow ® indwelling needle 22G supplied by Terumo Corp.) was connected, the porous membrane portion on the top end of the electrode (sensing portion 31 of the living body component-measuring sensor) was located about 1 mm on the inner side from the top end of the indwelling needle. The other end of the electrode was taken out from a hole formed in the wall of the extension tube and the hole was sealed with an epoxy resin. The indwelling needle was inserted into the femoral artery of a beagle dog (having a body weight of about 10 kg) under the artificial respiration and intravenous anesthesia, and the indwelling needle was connected to the connection portion of the extension tube so that the electrode was inserted into the indwelling needle. A polyvinyl chloride tube 12 having an inner diameter of 1 mm was connected to the three-way stop cock of the extension tube and an I.V. solution bag 6 was connected to this tube 12 through a high-resistance tube 5 (Intraflow ® supplied by Abbot Co.). A physiological saline solution containing sodium heparin in an amount of 4 u/ml as the heparin unit was in the I.V. solution bag. One end of the high-resistance tube was connected to a pressure transducer and the supply pressure of the heparin solution was adjusted to 300 mmHg.

Air in the heparin infusion line and the extension tube was expelled from the three-way stop cock, and continuous infusion of the heparin solution was initiated.

Hairs were sheared from the abdomen of the dog, and an Ag/AgCl disposable electrode (electrocardiographic electrode supplied by 3M Co.) was set as a reference electrode for an oxygen electrode and a temperature sensor was inserted into the gullet.

The oxygen electrode, reference electrode and temperature sensor were connected to a PO$_2$ monitor device (Model PO-2080 supplied by Mitsubishi Rayon Co.), and the measurement was started.

When PO$_2$ was monitored while the heparin solution was continuously infused in this state, the response characteristic was bad even if $FiO_2$ (oxygen concentration in the inspirated air) was changed, and the correlativity to the blood gas value obtained by performing the measurement on collected blood was bad. It was construed that the measurement was influenced by $PO_2$ of the heparin solution. However, if the polyvinyl tube 12 was placed between a solenoid (push type tubular solenoid supplied by Shindengen Kogyo K.K.) and a stand placed below the solenoid and compression/release was repeated at a frequency of one time per second along a length of 5 mm, a quick response to the change of $FiO_2$ was obtained and a good correlativity to the blood gas analysis value obtained by performing the measurement on collected blood was obtained. Namely, the correlative coefficient r was as high as 0.98 in the $PO_2$ range of 10 to 600 mmHg when the measurement was continuously conducted for 12 hours. This good correlativity was maintained during the measurement and the measurement could be carried out stably.

After the experiment, the oxygen electrode and indwelling needle were taken out from the artery and were examined with the naked eye. A formation of thrombs in the indwelling needle or on the porous membrane on the top end of the oxygen electrode was not observed.

EXAMPLE 2

The same polyvinyl chloride tube as used in Example 1 was disposed between a high-resistance tube 5 and a pressure transducer 7 and a solenoid was attached thereto. The polyvinyl chloride tube was instantaneously compressed at a frequency of one time per 5 seconds and quickly released. Other conditions were the same as described in Example 1.

The time required for the initial stabilization of the $PO_2$ value obtained by a monitor was as short as about 15 minutes, and a quick response to the change of $FiO_2$ was obtained and the continuous measurement could be conducted stably for 15 hours. The correlativity to the blood gas analysis value was good. In the blood pressure simultaneously monitored, some noises appeared owing to compression of the tube at a frequency of one time per 5 seconds, but the blood pressure was monitored without any practical trouble.

EXAMAPLE 3

A sensor 3 of an oxygen saturation degree-measuring apparatus for measuring the oxygen saturation degree in the blood from the absorbancy by using optical fibers (supplied by Oxymetrics Co., U.S.A.) was build in an extension tube 11 having at one end a connection portion 13 to be connected to an indwelling needle 2 and a three-way stop cock at the other end, and a Surflow ® indwelling needle 14G (supplied by Terumo Corp.) was used as the indwelling needle and the sensor was fixed to the extension tube so that when the indwelling needle was connected, the sensing portion 31 of the sensor was located about 3 mm on the inner side from the top end of the indwelling needle. A physiological saline solution containing sodium heparin in an amount of 4 u/ml as the heparin unit was charged in a syringe 42 having a capacity of 50 ml and the syringe was set to an infusion pump 41.

The indwelling needle was inserted into the ascending vena cava through the ingular vein in a beagle dog having a body weight of about 8 kg under artificial respiration and intravenous anesthesia, and the indwelling needle was connected to the connection portion of the extension tube so that the sensor was inserted into the indwelling needle.

The three-way stop cock of the extension tube having the sensor built therein was connected to the syringe filled with the heparin solution through an extension tube provided with a rotary type three-way stop cock, and a balloon 9 having an inner capacity of 0.1 ml formed of a silicone rubber such as a balloon to be attached to a pipette was connected to a non-used connection terminal of the rotary type three-way stop cock to form a line for infusing the heparin solution. Air in the infusion line and balloon was substituted with the heparin solution, and continuous infusion of the heparin solution at an injection rate of 2 ml/hr was initiated. By using an eccentric cam 8, the balloon was compressed for about 0.3 second at a frequency of one time per 2 seconds and was then quickly released. The eccentric cam was continuously operated so that the above-mentioned compression/release was repeated. In this state, the measurement was initiated. In the present experiment, the respirator was operated to change the oxygen saturation degree of the vein within the range of from about 10 to about 90%.

A good correlativity was observed (correlative coefficient of 0.98) between the value obtained at this measurement and the value of the oxygen saturation degree obtained by the measurement of collected blood. When the measurement was continuously conducted for 12 hours, a high measurement accuracy was obtained stably.

EXAMPLE 4

The procedures of Example 3 were repeated in the same manner except that a beagle dog having a body weight of 15 kg was used as the test animal, the Surflow ® indwelling needle 14G was inserted in the femoral vein so that when the indwelling needle was connected, the sensing portion of the sensor was located about 2 mm on the inner side from the top end of the indwelling needle, the three-way stop cock of the extension tube was connected to the syringe for infusing the heparin solution through the extension tube, and the extension tube was subjected to compression/release repeatedly along a length of 2 mm at a frequency of one time per second by changing the rotation direction of the eccentric cam according to the infusion of the heparting solution.

The measurement could be stably conducted for 15 hours continuously, and a good correlativity was observed between the obtained value and the value of the oxygen saturation degree measured in collected blood.

As is apparent from the foregoing description, when the instrument of the present invention is used, the sensing portion of the living body component-measuring sensor is inserted into the blood vessel and the blood component can be measured substantially continuously while maintaining the environment in the living body. Furthermore, since the sensing portion is located within the indwelling needle or indwelling catheter, reduction of the measurement accuracy owing to the contact of the sensing portion with the blood vessel wall is not caused. Moreover, since the interior of the indwelling needle or indwelling catheter was filled with the blood anticoagulant solution or a mixture thereof with blood in the normal state during the measurement, adhesion of coagulation products of the blood to the sensing portion of the sensor is prevented, and since the instrument has the mechanism for introducing blood into the sensing portion of the sensor within the indwelling needle or indwelling catheter and then discharging blood from the indwelling needle or indwelling catheter by infusion of the blood anticoagulant solution, the blood components can be measured with high accuracy and the instrument of the present invention is suitable for the continuous measurement conducted for a long time.

An ordinary line for infusion of a blood anticoagulant which is customarily used when an indwelling needle or the like is disposed can be utilized in the present invention, and therefore, it is not necessary to infuse the blood anticoagulant in an excessive amount.

Obviously, numerous modifications and variations of the present invention are possible in light of the above teachings. It is therefore to be understood that within the scope of the appended claims, the invention may be practiced otherwise than as specifically described herein.

We claim:

1. An instrument for measuring living body components, which comprises a (i) fine tube having at one end thereof a connection portion to be connected to an indwelling needle or indwelling catheter and an infusion portion, from which at least a solution of a blood anticoagulant can be infused; (ii) a fine linear sensor for measuring living body components, which is extended from the interior of the fine tube to the outside through the connection portion; and (iii) a mechanism for introducing blood at least into the interior of a fine tube portion of the indwelling needle or indwelling catheter intermittently or periodically when the indwelling needle or indwelling catheter is connected to the fine tube and kept in the blood vessel and then discharging blood into the blood vessel, said mechanism for introducing blood at least into the interior of the fine tube portion of the indwelling needle or indwelling catheter being a mechanism for intermittently or periodically applying a pressure to the wall of the fine tube and releasing said pressure, at least a part of the wall of the fine tube having an elasticity such that said part of the wall is deformed under application of an external pressure and then original shape of said part of the wall is restored when an external pressure different from said external pressure is applied or said external pressure is released; and a sensing portion of the sensor being located within the fine tube portion of the indwelling needle or indwelling cathether is connected to the connection portion of the fine tube.

2. An instrument for measuring living body components according to claim 1, wherein the sensing portion of the sensor is located at a point distant by 10 mm or less from the top end of the indwelling needle or indwelling catheter.

3. An instrument for measuring living body components, which comprises a (i) fine tube having at one end thereof a connection portion to be connected to an indwelling needle or indwelling catheter and an infusion portion, from which at least a solution of a blood anticoagulant can be infused; (ii) a fine linear sensor for measuring living body components, which is extended from the interior of the fine tube to the outside through the connection portion; and (iii) a mechanism for introducing blood at least into the interior of a fine tube portion of the indwelling needle or indwelling cather intermittently or periodically when the indwelling needle or indwelling cathether is connected to the fine tube and kept in the blood vessel and then discharging blood into the blood vessel, said mechanism for introducing blood at least into the interior of the fine tube portion of the indwelling needle or indwelling catheter comprising means for defining a volume-variable hollow portion connected only to the interior of the fine tube and a mechanism for applying a pressure to said hollow portion and releasing the pressure; and a sensing portion of the sensor being located within the fine tube portion of the indwelling needle or indwelling catheter when the indwelling needle or indwelling catheter is connected to the connection portion of the fine tube.

4. An instrument for measuring living body components according to claim 3, wherein the sensing portion of the sensor is located at a point distant by 10 mm or less from the top end of the indwelling needle or indwelling catheter.

5. An instrument for measuring living body components according to claim 3, wherein said means for defining a volume-variable hollow portion is a hollow balloon.

6. An instrument for measuring living body components according to claim 3, wherein said means for defining a volume-variable hollow portion is a syringe.

* * * * *